(12) United States Patent
Blaauw et al.

(10) Patent No.: US 10,285,590 B2
(45) Date of Patent: May 14, 2019

(54) INTRAOCULAR PRESSURE SENSOR WITH IMPROVED VOLTAGE REFERENCE CIRCUIT

(71) Applicant: THE REGENTS OF THE UNIVERSITY OF MICHIGAN, Ann Arbor, MI (US)

(72) Inventors: David T. Blaauw, Ann Arbor, MI (US); Zhiyoong Foo, Ann Arbor, MI (US); Gyouho Kim, Ann Arbor, MI (US); Qing Dong, Ann Arbor, MI (US); Dennis Sylvester, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/840,517

(22) Filed: Dec. 13, 2017

(65) Prior Publication Data

US 2018/0098696 A1 Apr. 12, 2018

Related U.S. Application Data

(63) Continuation-in-part of application No. 15/622,202, filed on Jun. 14, 2017.
(Continued)

(51) Int. Cl.
*A61B 3/16* (2006.01)
*G05F 3/24* (2006.01)
(Continued)

(52) U.S. Cl.
CPC .............. *A61B 3/16* (2013.01); *A61B 3/0016* (2013.01); *G05F 3/262* (2013.01);
(Continued)

(58) Field of Classification Search
CPC .......... G05F 3/262; G05F 1/462; G05F 1/463; G05F 1/618; A61B 3/16; A61B 3/0016;
(Continued)

(56) References Cited

U.S. PATENT DOCUMENTS 6,160,393 A 12/2000 Ahn et al.
6,589,198 B1 * 7/2003 Soltanpour ......... A61F 9/00781
604/151
(Continued)

FOREIGN PATENT DOCUMENTS

EP 2706426 3/2014

OTHER PUBLICATIONS

Y. Wang, Z. Zhu, J. Yao and Y. Yang, "A 0.45-V, 14.6-nW CMOS Subthreshold Voltage Reference With No Resistors and No BJTs," in IEEE Transactions on Circuits and Systems II: Express Briefs, vol. 62, No. 7, pp. 621-625.*
(Continued)

*Primary Examiner* — Jue Zhang
*Assistant Examiner* — Jye-June Lee
(74) *Attorney, Agent, or Firm* — Harness, Dickey & Pierce, P.L.C.

(57) ABSTRACT

An intraocular pressure sensor is presented that achieve very low power consumption. The intraocular pressure sensor takes the form of an implantable assembly configured to be implanted in an eye of a subject. Specifically, the implantable assembly is comprised of a capsular tension ring attached to a flexible printed circuit board. The flexible printed circuit board includes a cutout that is sized to encircle the pupil of the eye and is C shaped. One or more electrical components are also mounted onto the flexible printed circuit board. One such component is a voltage
(Continued)

reference generator that is implemented by a circuit which provides inherently low process variation and low power consumption.

16 Claims, 5 Drawing Sheets

Related U.S. Application Data

(60) Provisional application No. 62/349,731, filed on Jun. 14, 2016.

(51) Int. Cl.
*G05F 3/26* (2006.01)
*A61B 3/00* (2006.01)
*G05F 1/46* (2006.01)
*G05F 1/618* (2006.01)

(52) U.S. Cl.
CPC ............ *A61B 2560/0209* (2013.01); *A61B 2560/0219* (2013.01); *A61B 2560/045* (2013.01); *A61B 2562/028* (2013.01); *A61B 2562/0247* (2013.01); *A61B 2562/164* (2013.01); *A61B 2562/166* (2013.01); *G05F 1/462* (2013.01); *G05F 1/463* (2013.01); *G05F 1/618* (2013.01)

(58) Field of Classification Search
CPC .... A61B 2560/0209; A61B 2560/0219; A61B 2560/045; A61B 2560/0247; A61B 2560/028; A61B 2562/164; A61B 2560/166
See application file for complete search history.

(56) References Cited

U.S. PATENT DOCUMENTS

| | | | |
|---|---|---|---|
| 6,713,996 B2 | 3/2004 | Di Iorio | |
| 7,474,144 B2* | 1/2009 | Baumgartner | G05F 3/205 |
| | | | 323/315 |
| 7,486,129 B2 | 2/2009 | Pietri et al. | |
| 7,564,225 B2 | 7/2009 | Moraveji et al. | |
| 7,994,848 B2 | 8/2011 | Kothandaraman et al. | |
| 8,531,169 B2 | 9/2013 | Marinca | |
| 8,564,275 B2 | 10/2013 | Seok et al. | |
| 8,786,355 B2 | 7/2014 | Hao et al. | |
| 9,112,484 B1* | 8/2015 | Clark | H03K 3/0315 |
| 9,418,333 B2 | 8/2016 | Kim et al. | |
| 2011/0160853 A1* | 6/2011 | Scholten | A61B 3/16 |
| | | | 623/6.43 |
| 2013/0090534 A1* | 4/2013 | Burns | A61B 3/16 |
| | | | 600/301 |
| 2014/0084975 A1* | 3/2014 | Tang | H03L 7/0995 |
| | | | 327/156 |
| 2014/0275923 A1* | 9/2014 | Haffner | A61B 5/6867 |
| | | | 600/377 |
| 2014/0296687 A1* | 10/2014 | Irazoqui | A61B 3/16 |
| | | | 600/398 |
| 2014/0307513 A1* | 10/2014 | Chun | G11C 5/146 |
| | | | 365/189.09 |
| 2015/0045643 A1* | 2/2015 | Varel | A61B 3/16 |
| | | | 600/398 |
| 2016/0058324 A1* | 3/2016 | Cao | A61B 5/7282 |
| | | | 600/302 |
| 2017/0123444 A1* | 5/2017 | Tseng | G05F 1/59 |
| 2017/0357285 A1* | 12/2017 | Dong | G05F 3/262 |

OTHER PUBLICATIONS

L. Magnelli et al "A 2.6nW, 0.45 V Temperature-Compensated Subthreshold CMOS Voltage Reference" JSSC, (2011).

Y. Zeng et al "A 1.2NW, 2 IPPM/° C. Subthreshold CMOS Voltage Reference Without Resistors", IET Conference Proceedings Stevenage: The Institution of Engineering & Technology, (2013).

* cited by examiner

FIG. 2A  FIG. 2B

INTRAOCULAR PRESSURE SENSOR WITH IMPROVED VOLTAGE REFERENCE CIRCUIT

CROSS-REFERENCE TO RELATED APPLICATIONS

This application is a continuation-in-part of U.S. patent application Ser. No. 15/622,202 filed on Jun. 14, 2017 which claims the benefit of U.S. Provisional Application No. 62/349,731 filed on Jun. 14, 2016. The entire disclosure of the above applications are incorporated herein by reference.

FIELD

The present disclosure relates to an intraocular pressure sensor.

BACKGROUND

Intraocular pressure is the fluid pressure inside the eye. Intraocular pressure is an important measure in the diagnosis of patients at risk of glaucoma. Recently, implantable sensors have been developed to measure intraocular pressure inside the eye. Given the implantable nature of these sensors, it is imperative that sensors implantable in the eye consume low power to enable battery and energy harvesting to be miniaturized and obtain a small enough device to allow implantation. Therefore, it is desirable to provide an implantable intraocular pressure sensor having very low power consumption.

This section provides background information related to the present disclosure which is not necessarily prior art.

SUMMARY

This section provides a general summary of the disclosure, and is not a comprehensive disclosure of its full scope or all of its features.

An intraocular pressure sensor is presented that achieves very low power consumption. The intraocular pressure sensor takes the form of an implantable assembly configured to be implanted in an eye of a subject. Specifically, the implantable assembly is comprised of a capsular tension ring attached to a flexible printed circuit board. The flexible printed circuit board includes a cutout that is sized to encircle the pupil of the eye. One or more electrical components are also mounted onto the flexible printed circuit board.

In one embodiment, a pressure sensing element, a voltage reference generator, a power management unit and a controller are mounted to the implantable assembly. The pressure sensing element operates to output a measurable value, such that the measurable value changes in response to pressure applied to the pressure sensing element. The controller is interfaced with the pressure sensing element and receives the output from the pressure sensing element. In response to receiving the output, the controller converts the output to a digital form and stores the digital form of the output in a data store residing on the implantable assembly. The voltage reference generator generates a voltage that drives the controller and the power management unit is interconnected between the voltage reference generator and the controller.

In one aspect, the voltage reference generator includes a first metal-oxide semiconductor field-effect transistor (MOSFET) and a second MOSFET in a stacked arrangement, such that a body terminal of the first MOSFET is biased with a voltage that is different than voltage at a source terminal of the first MOSFET and voltage at a drain terminal of the first MOSFET. More specifically, the first MOSFET of the voltage reference generator has a source terminal, a drain terminal, a gate terminal and a body terminal, where the gate terminal of the first MOSFET is coupled to the source terminal of the first MOSFET; and the second MOSFET of the voltage reference generator has same type of charge carrier as the first MOSFET and is configured with the first MOSFET such that a reference voltage is generated at a node interconnecting the first MOSFET to the second MOSFET, where threshold voltage of the first MOSFET and threshold voltage of the second MOSFET are designed to be the same and the gate terminal of the second MOSFET is coupled to the drain terminal of the second MOSFET. The voltage reference generator may further include a bias circuit configured to bias the body terminal of the first MOSFET with a bias voltage that changes with temperature changes so that the reference voltage is temperature independent.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
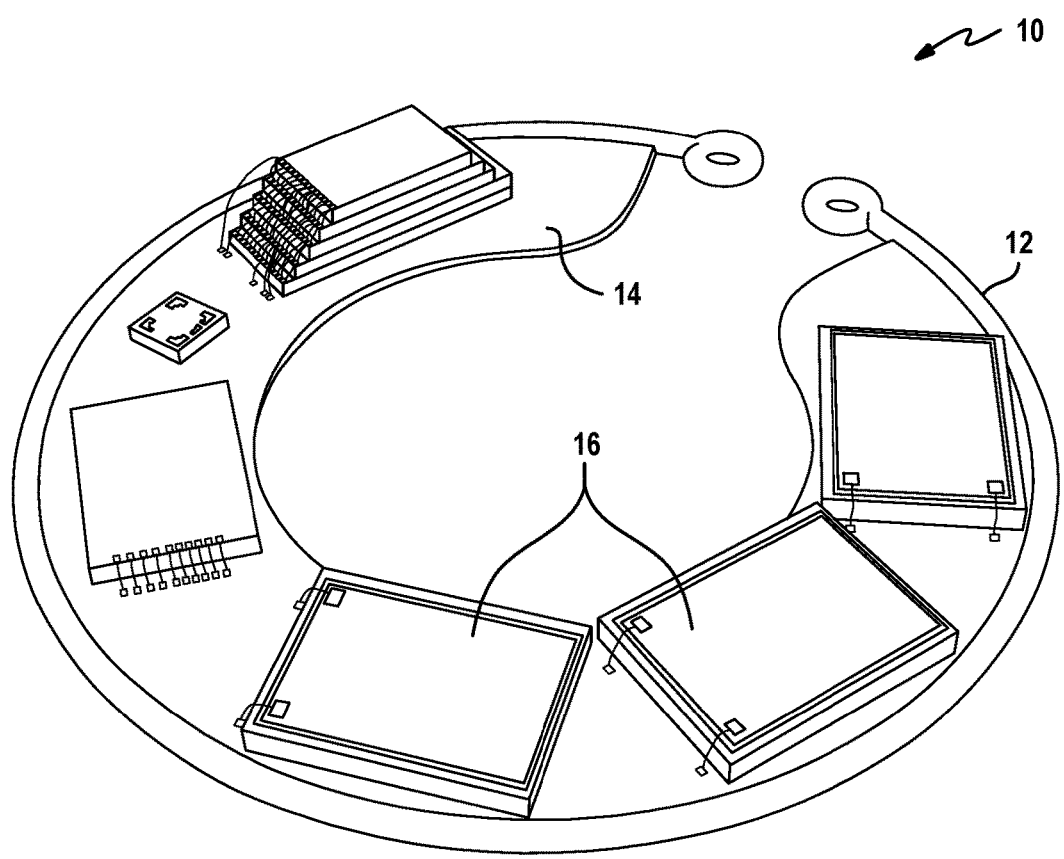
FIG. 1 is a perspective view of an intraocular pressure sensor.

FIG. 1 depicts an example embodiment for an intraocular pressure sensor 10 that is configured to be implanted in an eye of a subject. In an example embodiment, an implantable assembly is comprised of a capsular tension ring 12 coupled to a flexible printed circuit board 14. The flexible printed circuit board 14 may include a cutout that is sized to encircle the pupil of the eye. In addition, the printed circuit board has a "C" shape such that one section of the circular form remains open to the cutout. This allows one end of the capsular tension ring to be inserted through an incision in the eye and fed into the eye in circular motion to encircle the pupil of the eye. This allows the size of the necessary incision in the eye to be limited to only the width of the printed circuit board and not the width of the entire implantable assembly. One or more electrical components 16 are in turn mounted onto the flexible printed circuit board 14 such that the electrical components are mounted along periphery of the assembly and do not interfere with the subject's vision. For example, the electrical components may be epoxied onto the circuit board 14. For further details regarding an exemplary implantable assembly, reference may be had to the EYEMATE® sensor manufactured by Implandata Ophothalmic Products GmbH.

Figure 2:
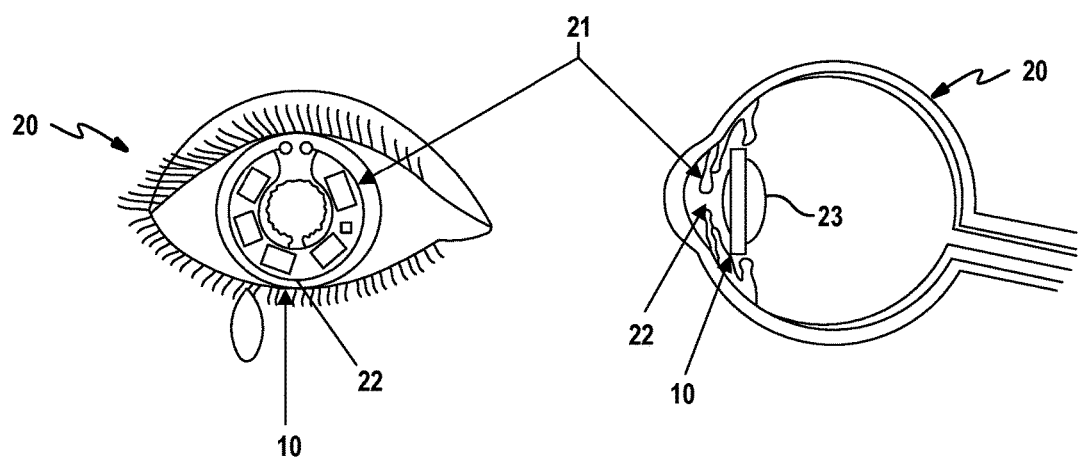
FIGS. 2A and 2B are a front view and a cross-section side view of an eye, respectively, illustrating the placement of the intraocular pressure sensor in the eye of a subject.

FIGS. 2A and 2B illustrate the placement of the intraocular pressure sensor 10 in the eye 20 of the subject. More specifically, the intraocular pressure sensor 10 is placed behind the iris 21 and pupil 22 of the eye in the posterior chamber. It is understood that different type of medical procedures may be used to place the intraocular pressure sensor 10 in the eye but such procedures fall outside the scope of this disclosure.

Figure 3:
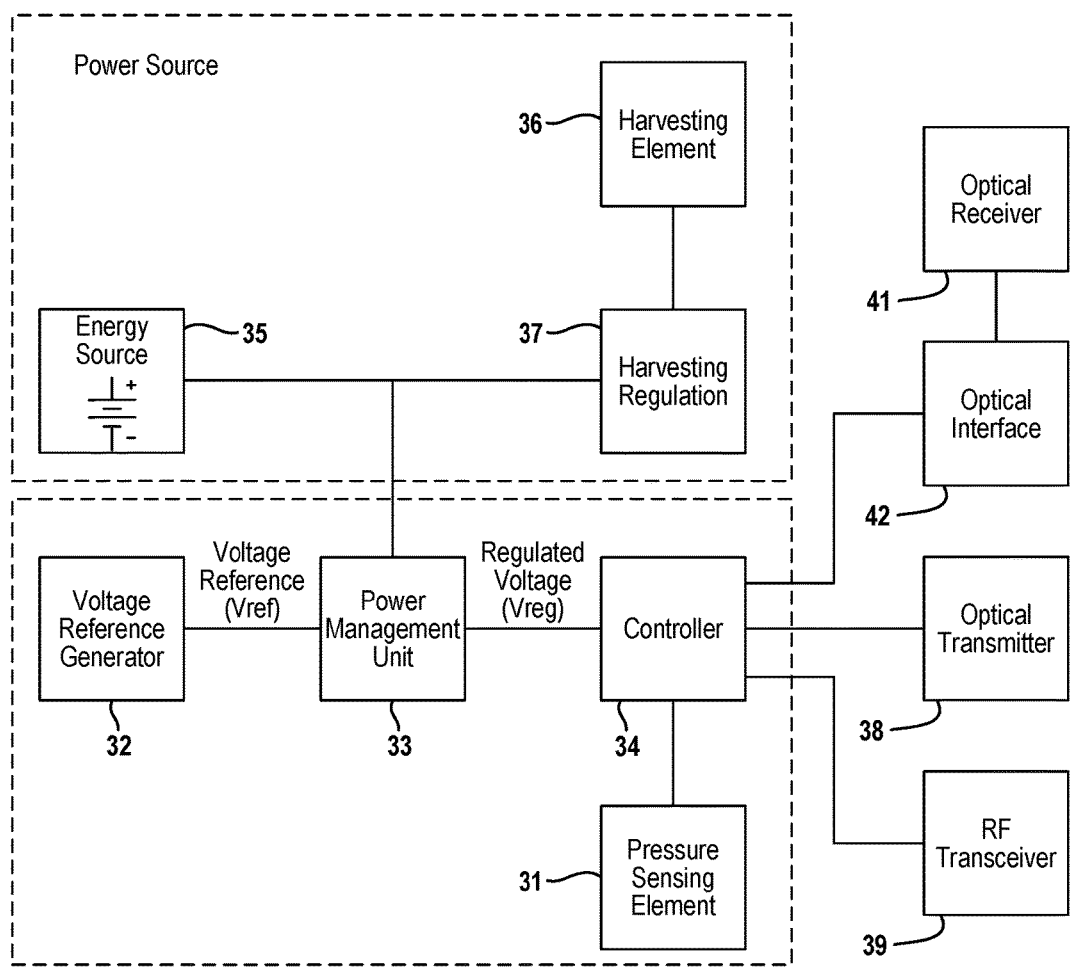
FIG. 3 is a block diagram of the components comprising the intraocular pressure sensor.

Components which comprise the intraocular pressure sensor 10 are further described in relation to FIG. 3. In the example embodiment, the intraocular pressure sensor 10 is comprised of a pressure sensing element 31, a voltage reference generator 32, a power management unit 33 and a controller 34. Each of these components is further described below. It is to be understood that these components are required, but that other components may be needed to control and manage the overall operation of the sensor.

The pressure sensing element 31 is attached to the implantable assembly and operates to output a measurable value (e.g., capacitance or resistance), such that the measurable value changes in response to pressure applied to the pressure sensing element. In one embodiment, the pressure sensing element is a piezoelectric membrane that changes resistance as it deflects due to the applied pressure. In another embodiment, it is a conductive membrane that covers a vacated cavity and causes the capacitance between the membrane and the cavity to change as the membrane deflects due to the applied pressure. Other types of pressure sensing elements also fall within the scope of this disclosure.

A controller 34 is interfaced with the pressure sensing element 31 and configured to receive the output from the pressure sensing element 31. In response to receiving the output, the controller 34 converts the output to a digital form and stores the digital form of the output in a data store (e.g., a transitory or non-transitory memory). In an exemplary embodiment, the controller 34 is implemented as a microcontroller. It should be understood that the logic for the controller 34 can be implemented in hardware logic, software logic, or a combination of hardware and software logic. In this regard, controller 34 can be or can include any of a digital signal processor (DSP), microprocessor, microcontroller, or other programmable device which are programmed with software implementing the above described methods. It should be understood that alternatively the controller is or includes other logic devices, such as a Field Programmable Gate Array (FPGA), a complex programmable logic device (CPLD), or application specific integrated circuit (ASIC). When it is stated that controller 34 performs a function or is configured to perform a function, it should be understood that controller 34 is configured to do so with appropriate logic (such as in software, logic devices, or a combination thereof).

The voltage reference generator 32 operates to generate a voltage that drives the controller 34. As will be further described below, the voltage reference generator 32 is implemented by a circuit that provides inherently low process variation and low power consumption. The power management unit 33 is interconnected between the voltage reference generator 32 and the controller 34. In one embodiment, the power management unit 33 is a voltage regulator circuit. The voltage regulator circuit receives a reference voltage from the voltage reference generator 32 and provides a stable voltage to the controller 34. Those skilled in the art will recognize that suitable regulator circuits are readily found in the art. In another embodiment, the power management unit 33 converts an input voltage within a 0.9-to-4V range to 3 fixed output voltages: 0.6V, 1.2V and 3.3V. Further details regarding such a unit are described by Wanyeong Jung et. al. in "A 60%-Efficiency 20 nW-500 µW Tri-Output Fully Integrated Power Management Unit with Environmental Adaptation and Load-Proportional Biasing for IoT Systems," IEEE International Solid-State Circuits Conference (ISSCC), February 2016 which is incorporated in its entirety herein.

The intraocular pressure sensor 10 also includes a power source. The power source supplies power to the power management unit 33. The power source may take different forms. In one form, the power source is a battery. In another form, the power source is comprised of a harvesting subsystem that charges a rechargeable energy storage device 35, such as a capacitor or a battery. The harvesting subsystem may include a harvesting element 36 (e.g., a photovoltaic cell) that generates electrical power and a regulator circuit 37 interfaced with the harvesting element. The regulator circuit converts the electrical power from the harvesting element to a suitable form for charging the rechargeable energy storage device 35. The rechargeable energy storage device 35 can in turn be used to supply power to one or more of the other components of the sensor.

One embodiment of the regulator circuit 27 is a switched-capacitor DC-DC converter which converts the voltage of the harvesting element 37 to the voltage for the energy storage device 35 through a series of voltage multiplications. Each voltage multiplication can be accomplished by constructing two inverter based ring oscillators, where the outputs of each inverter in one ring is coupled to the output of the corresponding inverter in the second ring. For further details regarding an exemplary switched-capacitor DC-DC converter, reference may be had to U.S. Patent Publication No. 2017/0170722 entitled "Self-oscillating Switched-Capacitor DC-DC Converter" and which is incorporated in its entirety by reference.

In some embodiments, the intraocular pressure sensor 10 may further include a communication interface. For example, the communication interface may be an LED or another type of light source serving as an optical transmitter 38. In another example, the communication interface may be an RF transmitter or transceiver 39. In either case, the controller 34 cooperatively operates with the optical transmitter or the RF transmitter to transmit the digital form of the output to a device located outside of the eye. In the case of the LED, the external device may be a photodetector, or in the case of the RF transmitter, the external device may be an RF receiver. It is readily understood that these are merely examples of the types of wireless interfaces that may be incorporated into the sensor.

Similarly, the intraocular pressure sensor 10 may include an optical communication receiver which allows communication from an external device to the sensor 10. In this case, an optical sensor 41 is interfaced via an optical interface 42 to the controller 34. The optical sensor may be a photo sensor or photo voltaic cell which transforms received light to an electrical signal. The controller 34 cooperatively operates with the optical communication interface 42 to receive a digital form of an input from a device located outside of the eye.

Figure 4:
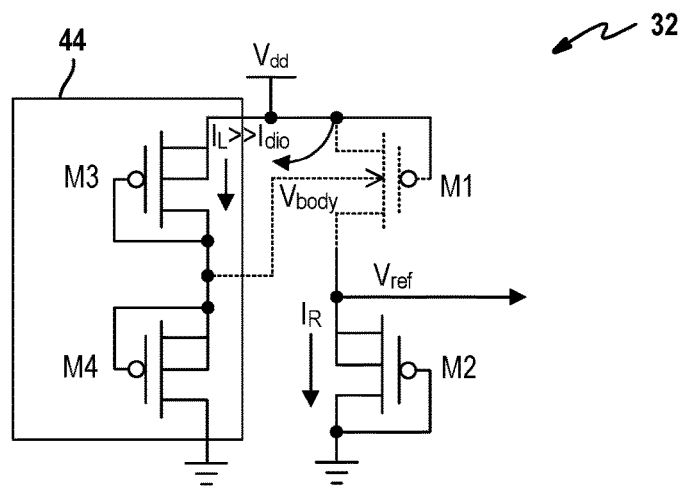
FIG. 4 shows a simplified circuit of proposed voltage reference circuit.

FIG. 4 depicts an example embodiment for the voltage reference circuit 32. The proposed voltage reference circuit is comprised of two metal-oxide semiconductor field-effect transistors (MOSFETs) M1, M2 in a stacked arrangement and a bias circuit 44. In the stacked arrangement, the two MOSFETs M1, M2 are configured with one of the source terminal and the drain terminal of the first MOSFET M1 coupled to a first supply voltage VDD, and the other of the source terminal and the drain terminal of the first MOSFET is coupled to one of the source terminal and the drain terminal of the second MOSFET M2. The other of the source terminal and the drain terminal of the second MOSFET M2 is coupled to a second supply voltage (e.g., ground). The first MOSFET M1 and the second MOSFET M2 have the same type of charge carrier and the particular terminal connections will depend upon the type of charge carrier as further described below.

Additionally, the gate terminal of the first MOSFET M1 is coupled to the source terminal of the first MOSFET M1 and the gate terminal of the second MOSFET M2 is coupled to the drain terminal of the second MOSFET M2. Of note, the body terminal of the first MOSFET M1 is biased with a voltage that is different than the voltage at either the source terminal or the drain terminal of the first MOSFET M1. It is also noted that the threshold voltage $V_{th1}$ of the first MOSFET M1 and threshold voltage $V_{th2}$ of the second MOSFET M2 are designed and manufactured to be the same.

In a first example embodiment, the first MOSFET M1 and second MOSFET M2 are p-type as seen in FIG. 4. In the stacked arrangement, source terminal of the first MOSFET M1 is electrically coupled to the upper supply voltage ($V_{dd}$) while the drain terminal of the first MOSFET M1 is electrically coupled to the source terminal of the second MOSFET M2 and the drain terminal of the second MOSFET M2 is electrically coupled to the lower supply voltage (e.g., ground). The reference voltage $V_{ref}$ is generated at an output node interconnecting the first MOSFET M1 to the second MOSFET M2.

In operation, the first MOSFET M1 is forward-biased and provides sub-threshold current flowing through the second MOSFET (i.e., bottom PMOS diode) M2. The second MOSFET M2 is in an off state. The current equations of M1 and M2 are expressed as in equation (1). By solving equation (1), $V_{ref}$ can be expressed as equation (3). As M1 and M2 are the same type of charge carrier (i.e, PMOS), the difference between $V_{th1}$ and $V_{th2}$ comes solely from the body bias effect of M1. Random $V_{th}$ mismatch is kept negligible by upsizing (e.g., >20 μm$^2$) of all 4 devices in this reference circuit.

$$I_R = u_p C_{ox} \frac{W_1}{L_1} n V_T^2 \exp\left(\frac{0 - V_{th1}}{mV_T}\right) = u_p C_{ox} \frac{W_2}{L_2} n V_T^2 \exp\left(\frac{0 - V_{ref} - V_{th2}}{mV_T}\right) \quad (1)$$

$$I_L = \quad (2)$$
$$u_p C_{ox} \frac{W_3}{L_3} n V_T^2 \exp\left(\frac{V_{body} - V_{dd} - V_{th3}}{mV_T}\right) = u_p C_{ox} \frac{W_4}{L_4} n V_T^2 \exp\left(\frac{0 - V_{th4}}{mV_T}\right)$$

$$V_{ref} = V_{th1} - V_{th2} + mV_T \ln\frac{W_1 L_2}{W_2 L_1} \quad (3)$$

$$= \gamma\left(\sqrt{2\phi_b - mV_T \ln\frac{W_4 L_3}{W_3 L_4}} - \sqrt{2\phi_b}\right) + mV_T \ln\frac{W_1 L_2}{W_2 L_1} \quad (4)$$

The bias circuit 42 is configured to output the voltage that biases the body terminal of the first MOSFET M1. In the example embodiment, the bias circuit 44 is comprised of transistors having the same type of charge carrier as the first MOSFET M1 and the second MOSFET M2. That is, the third MOSFET M3 and the fourth MOSFET M4 are p-type as well. More specifically, the third MOSFET M3 and the fourth MOSFET M4 are in a stacked arrangement, such that the drain terminal of the third MOSFET M3 is electrically coupled at a bias node to the source terminal of the fourth MOSFET M4. The bias node is also electrically coupled to the body terminal of the first MOSFET to supply the bias voltage thereto.

Figure 5:
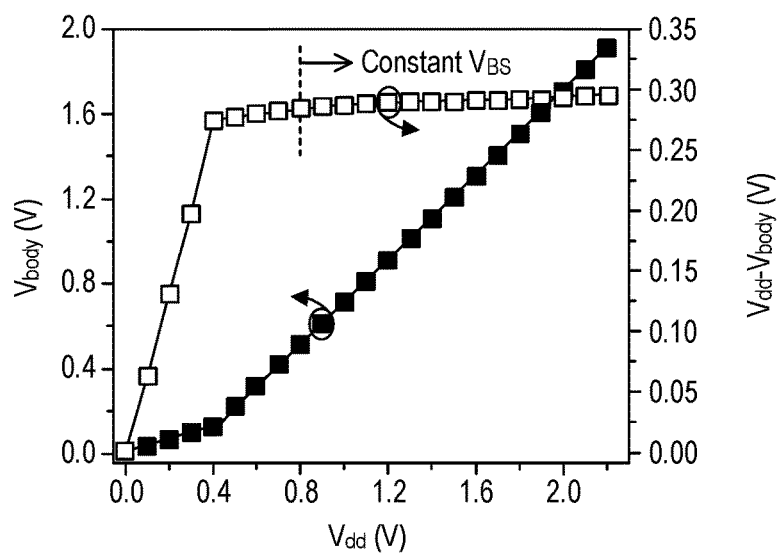
FIG. 5 is a graph showing how $V_{body}$ tracks $V_{dd}$ change and creates constant $V_{BS}$ for the first MOSFET.

In operation, the third MOSFET M3 and the fourth MOSFET M4 generate the required body bias for first MOSFET M1. More specifically, the fourth MOSFET M4 is an off-state PMOS; whereas, the third MOSFET is a PMOS diode. The current equations of M3 and M4 are expressed above in equation (2). As the third MOSFET and the fourth MOSFET M3 and M4 are also the same type of PMOS, $V_{th3}$ and $V_{th4}$ are essentially identical. The combination of the third MOSFET M3 and the fourth MOSFET M4 provides a body-bias voltage $V_{body}$ that tracks $V_{dd}$ and creates a constant $V_{BS}$ ($V_{body}$-$V_{dd}$) for first MOSFET M1 as shown in FIG. 5. If the current through third MOSFET M3 ($I_L$) is much larger than the parasitic diode current ($I_{dio}$) from the source to the N-well of M1, $V_{ref}$ can be expressed by equation (4). The left term of Equation (4) is complementary to temperature; whereas, the right term is proportional to temperature. With proper sizing of the four transistors, the first-order temperature dependency can be cancelled out. That is, the bias is circuit can be configured to bias the body terminal of the first MOSFET with a bias voltage that changes with temperature changes so that the reference voltage is temperature independent. Moreover, the threshold voltage $V_{th}$ does not play a role in equation (4) because each pair (M1/M2 and M3/M4) uses the same type of PMOS, thus significantly reducing process variation. Since $I_{dio}$ is not well modeled, $I_L$ is designed to be three orders of magnitude larger than $I_{dio}$ to minimize the effect of $I_{dio}$. Proper sizing of these transistors can be determined using a global optimization tool.

Figure 6:
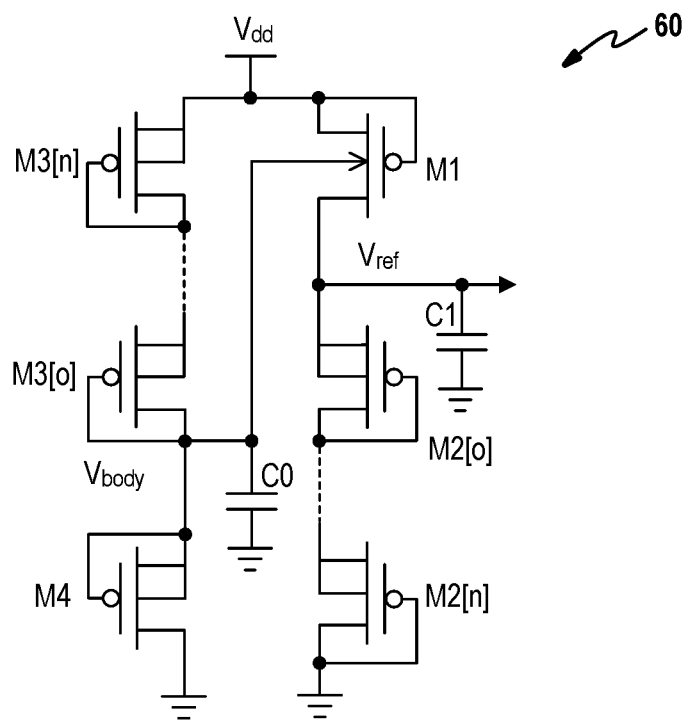
FIG. 6 is a schematic of the proposed voltage reference circuit with stacked PMOS diodes.

Variants of this proposed design are contemplated by this disclosure. Referring to FIG. 6, two or more stacked diodes can replace the second MOSFET M2 and the third MOSFET M3 to generate a higher reference voltage. Multiple voltage reference levels can be generated in this manner. In FIG. 6, three stages of PMOS diodes are used in the design to realize an approximately 1V output reference voltage. MIM capacitors C0 and C1 (both set to 1.78 pF) are used to isolate the reference voltage from high-frequency power supply noise. Except with respect to the differences discussed herein, the voltage reference circuit 60 may be substantially the same voltage reference circuit 32 described above.

Figure 7:
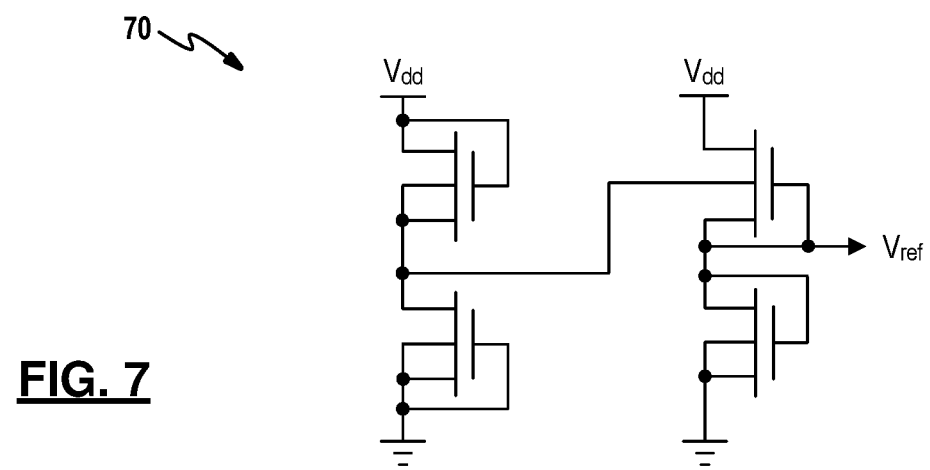
FIG. 7 is a schematic of a variant of the voltage reference circuit implemented with n-type transistors.

FIG. 7 depicts a variant of the voltage reference circuit 70 employing n-type transistors. In this variant, the drain terminal of the first MOSFET M1 is electrically coupled to the upper supply voltage while the source terminal of the first MOSFET M1 is electrically coupled to the drain terminal of the second MOSFET M2. The source terminal of the second MOSFET M2 is electrically coupled to the lower supply voltage, where magnitude of the upper supply voltage is larger than the lower supply voltage. Except with respect to the differences discussed herein, the voltage reference circuit 70 may be substantially the same voltage reference circuit 32 described above.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An intraocular pressure sensor, comprising:
an implantable assembly configured to be implanted in an eye of a subject;
a pressure sensing element attached to the implantable assembly and operable to output a measurable value, wherein the measurable value changes in response to pressure applied to the pressure sensing element;
a controller interfaced with the pressure sensing element and configured to receive the output from the pressure sensing element;
a voltage reference generator attached to the implantable assembly and operable to generate a voltage that drives the controller, wherein the voltage reference generator includes a first metal-oxide semiconductor field-effect transistor (MOSFET) and a second MOSFET in a stacked arrangement, such that a body terminal of the first MOSFET is biased with a voltage that is different than voltage at a source terminal of the first MOSFET and voltage at a drain terminal of the first MOSFET,
wherein the first MOSFET of the voltage reference generator has a gate terminal that is directly coupled to the source terminal of the first MOSFET,
wherein the second MOSFET of the voltage reference generator has same type of charge carrier as the first MOSFET and is configured with the first MOSFET such that a reference voltage is generated at a node interconnecting the first MOSFET to the second MOSFET, where threshold voltage of the first MOSFET and threshold voltage of the second MOSFET are designed to be the same and the gate terminal of the second MOSFET is directly coupled to the drain terminal of the second MOSFET; and
a voltage regulator attached to the implantable assembly and interconnected between the voltage reference generator and the controller.

2. The intraocular pressure sensor of claim 1 wherein the implantable assembly includes a capsular tension ring attached to a flexible printed circuit board.

3. The intraocular pressure sensor of claim 1 wherein the pressure sensing element is further defined as one of a piezoelectric membrane and a conductive membrane.

4. The intraocular pressure sensor of claim 1 wherein the controller, in response to receiving the output, converts the output to a digital form and stores the digital form of the output in a data store residing on the implantable assembly.

5. The intraocular pressure sensor of claim 4 further comprises a communication interface attached to the implantable assembly, where the controller cooperatively operates with the communication interface to transmit the digital form of the output to a device located outside of the eye.

6. The intraocular pressure sensor of claim 1 further comprises a power source attached to the implantable assembly, where the power source supplies power to the voltage regulator.

7. The intraocular pressure sensor of claim 1 wherein the controller is further defined as a microcontroller.

8. The intraocular pressure sensor of claim 1 wherein the voltage reference generator further includes a bias circuit configured to bias the body terminal of the first MOSFET with a bias voltage that changes with temperature changes so that the reference voltage is temperature independent.

9. An intraocular pressure sensor, comprising:
a capsular tension ring;
a flexible circuit board coupled to the capsular tension ring;
a pressure sensing element attached to the flexible circuit board and operable to output a measurable value, wherein the measurable value changes in response to pressure applied to the pressure sensing element;
a controller attached to the flexible circuit board and configured to receive the output from the pressure sensing element;
a voltage reference generator attached to the flexible circuit board and operable to generate an input voltage, wherein the voltage reference generator includes a first metal-oxide semiconductor field-effect transistor (MOSFET) and a second MOSFET in a stacked arrangement, such that a body terminal of the first MOSFET is biased with a voltage that is different than voltage at a source terminal of the first MOSFET and voltage at a drain terminal of the first MOSFET
wherein the first MOSFET of the voltage reference generator has a gate terminal that is directly coupled to the source terminal of the first MOSFET,
wherein the second MOSFET of the voltage reference generator has same type of charge carrier as the first MOSFET and is configured with the first MOSFET such that a reference voltage is generated at a node interconnecting the first MOSFET to the second MOSFET, where threshold voltage of the first MOSFET and threshold voltage of the second MOSFET are designed to be the same and the gate terminal of the second MOSFET is directly coupled to the drain terminal of the second MOSFET; and
a power management unit attached to the flexible circuit board and configured to receive the input voltage from the voltage reference generator.

10. The intraocular pressure sensor of claim 9 wherein the flexible circuit board has a cutout sized to encircle pupil of an eye.

11. The intraocular pressure sensor of claim 10 wherein the pressure sensing element is further defined as one of a piezoelectric membrane and a conductive membrane.

12. The intraocular pressure sensor of claim 11 wherein the controller, in response to receiving the output, converts the output to a digital form and stores the digital form of the output in a memory residing on the implantable assembly.

13. The intraocular pressure sensor of claim 12 further comprises an optical transmitter interface with the controller and attached to the implantable assembly, where the controller cooperatively operates with the optical transmitter to transmit the digital form of the output to a device located outside of the eye.

14. The intraocular pressure sensor of claim 13 further comprises a battery attached to the implantable assembly and the battery is configured to supply power to the power management unit.

15. The intraocular pressure sensor of claim 14 further comprises a photovoltaic cell attached to the implantable assembly and a regulator circuit electrically coupled between the photovoltaic cell and the battery.

16. The intraocular pressure sensor of claim 9 wherein the voltage reference generator further includes a bias circuit configured to bias the body terminal of the first MOSFET with a bias voltage that changes with temperature changes so that the reference voltage is temperature independent.

* * * * *